(12) United States Patent
Josso

(10) Patent No.: US 8,420,062 B2
(45) Date of Patent: Apr. 16, 2013

(54) NON-AEROSOL/AEROSOL DISPENSING OF SUNSCREEN SPRAYS COMPRISING SPHERICAL POROUS SILICA MICROPARTICLES

(75) Inventor: Martin Josso, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 12/792,835

(22) Filed: Jun. 3, 2010

(65) Prior Publication Data

US 2010/0239677 A1 Sep. 23, 2010

Related U.S. Application Data

(63) Continuation of application No. 10/717,523, filed on Nov. 21, 2003, now abandoned.

(60) Provisional application No. 60/449,574, filed on Feb. 26, 2003.

(30) Foreign Application Priority Data

Nov. 21, 2002 (FR) ..................... 02 14599

(51) Int. Cl.
| | |
|---|---|
| *A61K 8/00* | (2006.01) |
| *A61K 8/04* | (2006.01) |
| *A61K 8/06* | (2006.01) |
| *A61K 8/49* | (2006.01) |
| *A61K 9/14* | (2006.01) |
| *A61Q 5/00* | (2006.01) |
| *A61Q 17/02* | (2006.01) |
| *A61Q 17/04* | (2006.01) |
| *A61Q 19/04* | (2006.01) |

(52) U.S. Cl.
USPC .............. 424/60; 424/59; 424/70.9; 424/401; 424/489; 424/DIG. 1

(58) Field of Classification Search .................... 424/59, 424/50, 70.9, 401, 489, DIG. 1
See application file for complete search history.

(56) References Cited

U.S. PATENT DOCUMENTS

| | | | |
|---|---|---|---|
| 5,914,102 | A | 6/1999 | Fowler et al. |
| 5,939,079 | A | 8/1999 | Le Royer et al. |
| 6,004,567 | A | 12/1999 | Marchi-Lemann et al. |
| 6,171,602 | B1 | 1/2001 | Roman |
| 6,258,857 | B1 | 7/2001 | Iijima et al. |
| 2001/0036466 | A1 | 11/2001 | Roulier et al. |

FOREIGN PATENT DOCUMENTS

| | | |
|---|---|---|
| EP | 0 679 382 A1 | 11/1995 |
| EP | 0 968 703 A1 | 1/2000 |
| JP | 11222420 | 8/1999 |
| JP | 2002047164 | 2/2002 |

OTHER PUBLICATIONS

Search Report issued in French Priority Counterpart corresponding to FR 02/14599, dated Aug. 13, 2003.

*Primary Examiner* — James H. Alstrum-Acevedo
(74) *Attorney, Agent, or Firm* — Buchanan Ingersoll & Rooney PC

(57) ABSTRACT

Nonaerosol/atomizer pumps or aerosol dispensers comprise (A) a reservoir confining at least one vaporizable sunscreen composition suited for UV-photoprotecting the skin and/or hair against the damaging effects of UV radiation, the at least one vaporizable sunscreen composition comprising (1) a UV-photoprotecting amount of at least one UV-sunscreen and (2) an SPF-enhancing amount of generally spherical silica microparticles, formulated into (3) a topically applicable, cosmetically acceptable carrier therefor, and (B) at least one agent for pressurizing the at least one vaporizable sunscreen composition into a spray of fine sunscreen particles.

56 Claims, No Drawings

NON-AEROSOL/AEROSOL DISPENSING OF SUNSCREEN SPRAYS COMPRISING SPHERICAL POROUS SILICA MICROPARTICLES

CROSS-REFERENCE TO PRIORITY/PROVISIONAL APPLICATIONS

This application is a continuation of application Ser. No. 10/717,523 which claims priority under 35 U.S.C. §119 of FR 02/14599, filed Nov. 21, 2002, and of provisional application Ser. No. 60/449,574, filed Feb. 26, 2003, each of which is hereby expressly incorporated by reference.

BACKGROUND OF THE INVENTION

1. Technical Field of the Invention

The present invention relates to a pressurizing device or dispenser comprising at least (A) a reservoir containing at least one composition intended for protecting the skin and/or the hair against ultraviolet radiation, said at least one composition which comprises, in a cosmetically acceptable aqueous carrier, at least: (a) a photoprotective system capable of screening out UV radiation; (b) generally spherical microparticles of porous silica; and (B) means which make it possible to put the at least one composition under pressure.

2. Description of Background/Related/Prior Art

It is known that light radiation having wavelengths of between 280 nm and 400 nm allows tanning of the human epidermis, and that radiation having wavelengths of between 280 nm and 320 nm, known by the name UV-B radiation, causes erythemas and skin burns which can impede the development of natural tanning; this UV-B radiation should therefore be screened out.

It is also known that UV-A rays having wavelengths of between 320 nm and 400 nm, which cause tanning of the skin, are capable of inducing its impairment, in particular in the case of a sensitive skin or of a skin continually exposed to solar radiation. UV-A rays cause in particular a loss of elasticity of the skin and the appearance of wrinkles which lead to premature skin aging. They promote the onset of the erythematous reaction or amplify this reaction in some subjects and may even be responsible for phototoxic or photoallergic reactions. It is therefore desirable also to screen out UV-A radiation.

Many cosmetic compositions intended for photoprotecting (UV-A and/or UV-B) the skin are known to this art.

These anti-sun compositions are quite often provided in the form of an oil-in-water type emulsion (that is to say a cosmetically acceptable carrier consisting of an aqueous dispersing continuous phase and an oily dispersed discontinuous phase) which contains, in various concentrations, one or more lipophilic and/or hydrophilic conventional organic screening agents capable of selectively absorbing harmful UV radiation, these screening agents (and their quantities) being selected according to the desired sun protection factor, the sun protection factor (SPF) mathematically expressing the ratio of the dose of UV radiation necessary to achieve the erythematogenic threshold with the UV screening agent to the dose of UV radiation necessary to achieve the erythematogenic threshold without UV screening agent.

Accordingly, an increasing need exists for anti-sun or sunscreen products having a high protection index. High protection indices can be obtained by incorporating more screening agents in high concentrations. This can not always be done since the addition of large quantities of screening agents considerably increases the cost of the anti-sun formulations and the risks of skin irritation.

Anti-sun/sunscreen products provided in spray form are increasingly sought by consumers because of their ease of use and their cosmetic pleasantness.

Unlike conventional anti-sun milks and creams, it is particularly difficult to obtain anti-sun compositions in spray form having a high protection index.

SUMMARY OF THE INVENTION

After considerable research, it has now surprisingly and unexpectedly been determined that including spherical microparticles of porous silica in a pressurizing device confining a composition containing at least one UV radiation screening system, it is possible to obtain an anti-sun/sunscreen composition having protection indices higher than those which may be obtained with the same photoprotective system alone.

This discovery forms the basis of the present invention.

DETAILED DESCRIPTION OF BEST MODE AND SPECIFIC/PREFERRED EMBODIMENTS OF THE INVENTION

Thus, the present invention features a pressurizing device comprising at least (A) a reservoir containing at least one composition intended for protecting the skin and/or the hair against ultraviolet radiation, said at least one composition which comprises, in a cosmetically acceptable aqueous carrier, at least: (a) a photoprotective system capable of screening out UV radiation; (b) spherical microparticles of porous silica; and (B) means which make it possible to put said at least one composition under pressure.

According to the invention, the expression photoprotective system capable of screening out UV radiation is understood to denote generally any compound or any combination of compounds which, by mechanisms known per se of absorption and/or reflection and/or diffusion of UV-A and/or UV-B radiation, makes it possible to prevent, or at least limit, the coming of the said radiation into contact with a surface (skin, hair) to which this or these compounds have been applied. In other words, these compounds may be UV absorbing photoprotective organic screening agents or inorganic (nano)pigments diffusing and/or reflecting UV, and mixtures thereof.

The present invention also features the use of spherical microparticles of porous silica in a vaporizable composition comprising, in a cosmetically acceptable aqueous carrier, at least one photoprotective system capable of screening out UV radiation, as agent which makes it possible to increase the sun protection factor (SPF).

According to the invention, the expression "vaporizable composition" is understood to denote in general any composition which is capable of producing, under pressure in an appropriate device or dispenser, fine particles.

Other characteristics, aspects and advantages of the present invention will emerge on reading the detailed description which follows.

The spherical microparticles of porous silica in accordance with the invention preferably have a mean particle size ranging from 0.5 μm to 20 μm and more particularly from 3 μm to 15 μm.

They preferably have a specific surface ranging from 50 to 1,000 m$^2$/g and more particularly from 150 to 800 m$^2$/g.

They preferably have a specific pore volume ranging from 0.5 to 5 ml/g and more particularly from 1 to 2 ml/g.

By way of example of microbeads of porous silica, it is possible to use the following commercial products:
Silica Beads SB 150 from Myoshi
Sunsphere H-51 from Asahi Glass
Sunsil 130 from Sunjin
Spherica P-1500 from Ikeda Corporation
Sylosphere from Fuji Silysia.

The spherical microparticles of porous silica in accordance with the present invention are used in the compositions in accordance with the invention at concentrations preferably ranging from 0.1% to 10% by weight relative to the total weight of the composition and more particularly from 0.2% to 5% by weight.

According to the invention, the photoprotective system may consist of one or more organic screening agents and/or one or more inorganic (nano)pigments.

The organic screening agents are chosen in particular from anthranilates; cinnamic derivatives; dibenzoylmethane derivatives; salicylic derivatives, camphor derivatives; triazine derivatives such as those described in U.S. Pat. No. 4,367,390, EP-863,145, EP-517,104, EP-570,838, EP-796,851, EP-775,698, EP-878,469, EP-933,376, EP-507,691, EP-507,692, EP-790,243 and EP-944,624; benzophenone derivatives; $\beta,\beta'$-diphenyl acrylate derivatives; benzotriazole derivatives; benzimidazole derivatives; imidazolines; bis-benzoazolyl derivatives as described in EP-669,323 and U.S. Pat. No. 2,463,264; p-aminobenzoic acid (PABA) derivatives; methylenebis(hydroxyphenylbenzotriazole) derivatives as described in U.S. Pat. Nos. 5,237,071, 5,166,355, GB-2,303,549, DE-1,972,6 184 and EP-893,119; benzoxazole derivatives as described in EP-0-832,642, EP-1-027,883, EP-1-300,137 and DE-10-162,844; screening polymers and screening silicones such as those described in particular in WO 93/04665; dimers derived from $\alpha$-alkylstyrene such as those described in DE-19,855,649; 4,4-diarylbutadienes such as those described in E-0-967,200, DE-19-746,654, DE-19-755,649, EP-A-1008586, EP-1-133,980 and EP-133,981 and mixtures thereof.

As examples of organic screening agents which are active in the UV-A and/or UV-B range, there may be mentioned those designated below under their INCI name:

Para-Aminobenzoic Acid Derivatives:
PABA,
Ethyl PABA,
Ethyl Dihydroxypropyl PABA,
Ethylhexyl Dimethyl PABA sold in particular under the name "ESCALOL 507" by ISP,
Glyceryl PABA,
PEG-25 PABA sold under the name "UVINUL P25" by BASF,
Salicylic Derivatives:
Homosalate sold under the name "Eusolex HMS" by Rona/EM Industries,
Ethylhexyl Salicylate sold under the name "NEO HELIOPAN OS" by Haarmann and REIMER,
Dipropyleneglycol Salicylate sold under the name "DIPSAL" by SCHER,
TEA Salicylate, sold under the name "NEO HELIOPAN TS" by Haarmann and REIMER,
Dibenzoylmethane Derivatives:
Butyl Methoxydibenzoylmethane sold in particular under the trademark "PARSOL 1789" by HOFFMANN LA ROCHE,
Isopropyl Dibenzoylmethane,
Cinnamic Derivatives:
Ethylhexyl Methoxycinnamate sold in particular under the trademark "PARSOL MCX" by HOFFMANN LA ROCHE,
Isopropyl Methoxy cinnamate,
Isoamyl Methoxy cinnamate sold under the trademark "NEO HELIOPAN E 1000" by HAARMANN and REIMER,
Cinoxate,
DEA Methoxycinnamate,
Diisopropyl Methylcinnamate,
Glyceryl Ethylhexanoate Dimethoxycinnamate,
$\beta,\beta'$-Diphenyl Acrylate Derivatives:
Octocrylene sold in particular under the trademark "UVINUL N539" by BASF,
Etocrylene, sold in particular under the trademark "UVINUL N35" by BASF,
Benzophenone Derivatives:
Benzophenone-1 sold under the trademark "UVINUL 400" by BASF,
Benzophenone-2 sold under the trademark "UVINUL D50" by BASF,
Benzophenone-3 or Oxybenzone, sold under the trademark "UVINUL M40" by BASF,
Benzophenone-4 sold under the trademark "UVINUL MS40" by BASF,
Benzophenone-5,
Benzophenone-6 sold under the trademark "Helisorb 11" by Norquay,
Benzophenone-8 sold under the trademark "Spectra-Sorb UV-24" by American Cyanamid,
Benzophenone-9 sold under the trademark "UVINUL DS-49" by BASF,
Benzophenone-12,
n-Hexyl 2-(4-diethylamino-2-hydroxybenzoyl)benzoate,
Benzylidenecamphor Derivatives:
3-Benzylidene camphor manufactured under the name "MEXORYL SD" by CHIMEX,
4-Methylbenzylidene camphor sold under the name "EUSOLEX 6300" by MERCK,
Benzylidene Camphor Sulphonic Acid manufactured under the name "MEXORYL SL" by CHIMEX,
Camphor Benzalkonium Methosulphate manufactured under the name "MEXORYL SO" by CHIMEX,
Terephthalylidene Dicamphor Sulphonic Acid manufactured under the name "MEXORYL SX" by CHIMEX,
Polyacrylamidomethyl Benzylidene Camphor manufactured under the name "MEXORYL SW" by CHIMEX,
Benzimidazole Derivatives:
Phenylbenzimidazole Sulphonic Acid sold in particular under the trademark "EUSOLEX 232" by MERCK, Disodium Phenyl Dibenzimidazole Tetra-sulphonate sold under the trademark "NEO HELIOPAN AP" by Haarmann and REIMER,
Triazine Derivatives:
Anisotriazine sold under the trademark "TINOSORB S" by CIBA SPECIALTY CHEMICALS,
Ethylhexyl triazone sold in particular under the trademark "UVINUL T150" by BASF,
Diethylhexyl Butamido Triazone sold under the trademark "UVASORB HEB" by SIGMA 3V,
2,4,6-Tris(diisobutyl 4'-aminobenzalmalonate)-s-triazine,
Benzotriazole Derivatives:
Drometrizole Trisiloxane sold under the name "Silatrizole" by RHODIA CHIMIE, Methylene bis-Benzotriazolyl Tetramethylbutylphenol, sold in solid form under the trademark "MIXXIM BB/100" by FAIRMOUNT CHEMICAL or in micronized form in aqueous dispersion under the trademark "TINOSORB M" by CIBA SPECIALTY CHEMICALS, Anthranilic Derivatives:
Menthyl anthranilate sold under the trademark "NEO HELIOPAN MA" by Haarmann and REIMER, Imidazoline Derivatives:
Ethylhexyl Dimethoxybenzylidene Dioxoimidazoline Propionate, Benzalmalonate Derivatives:
Polyorganosiloxane with benzalmalonate functional groups as the product Polysilicone-15 sold under the trademark "PARSOL SLX" by HOFFMANN LA ROCHE, 4,4-Diarylbutadiene Derivatives:
1,1-Dicarboxy-(2,2'-dimethylpropyl)-4,4-diphenylbutadiene Benzoxazole Derivatives:
2,4-bis-[5-1(diméthylpropyl)benzoxazol-2-yl-(4-phenyl)-imino]-6-(2-ethylhexyl)-imino-1,3,5-triazine sold under the trademark Uvasorb K2A by Sigma 3V; and mixtures thereof.

The organic screening agents which are more particularly preferred are chosen from the following compounds:
Ethylhexyl Salicylate,
Butyl Methoxydibenzoylmethane,
Ethylhexyl Methoxycinnamate,
Octocrylene,
Phenylbenzimidazole Sulphonic Acid,
Benzophenone-3,
Benzophenone-4,
Benzophenone-5,
n-Hexyl 2-(4-diethylamino-2-hydroxybenzoyl)benzoate,
4-Methylbenzylidene camphor,
Terephthalylidene Dicamphor Sulphonic Acid,
Disodium Phenyl Dibenzimidazole Tetra-sulphonate,
2,4,6-Tris(diisobutyl 4'-aminobenzalmalonate)-s-triazine,
Anisotriazine,
Ethylhexyl triazone,
Diethylhexyl Butamido Triazone,
Methylene bis-Benzotriazolyl Tetramethylbutylphenol,
Drometrizole Trisiloxane,
Polysilicone-15,
1,1-Dicarboxy-(2,2'-dimethylpropyl)-4,4-diphenyl-butadiene,
2,4-bis-[5-1(diméthylpropyl)benzoxazol-2-yl-(4-phenyl)-imino]-6-(2-ethylhexyl)-imino-1,3,5-triazine sold under and mixtures thereof.

The inorganic screening agents are chosen from pigments or nanopigments (mean primary particle size: generally between 5 nm and 100 nm, preferably between 10 nm and 50 nm) of metal oxides, coated or otherwise, such as for example nanopigments of titanium oxide (amorphous or crystallized in rutile and/or anatase form), of iron oxide, of zinc oxide, of zirconium oxide or of cerium oxide which are all UV photoprotective agents well known per se. Conventional coating agents are moreover alumina and/or aluminum stearate. Such coated or uncoated nanopigments of metal oxides are described in particular in EP-518,772 and EP-518,773.

The photoprotective system according to the invention is generally present in the compositions according to the invention in an amount ranging from 0.1% to 30% by weight and preferably from 0.5% to 15% by weight, relative to the total weight of the composition.

The vaporizable compositions in accordance with the invention are applied to the skin or the hair in the form of fine particles by means pressurizing devices. The devices in accordance with the invention are well known to persons skilled in the art and comprise nonaerosol or "atomizer" pumps, aerosol containers comprising propellants and aerosol pumps using compressed air as propellant. The latter are described in U.S. Pat. Nos. 4,077,441 and 4,850,517 (which form an integral part of the content of the description).

The compositions packaged as an aerosol in accordance with the invention contain in general conventional propelling agents such as for example the hydrofluorinated compounds dichlorodifluoromethane, difluoroethane, dimethyl ether, isobutane, n-butane, propane or trichlorofluoromethane. They are preferably present in quantities ranging from 15% to 50% by weight relative to the total weight of the composition.

The compositions according to the invention may also contain agents for artificially bronzing and/or tanning the skin (self-tanning agents).

The self-tanning agents are generally chosen from mono- or polycarbonyl compounds such as for example isatin, alloxan, ninhydrin, glyceraldehyde, mesotartaric aldehyde, glutaraldehyde, erythrulose, pyrazolin-4,5-dione derivatives as described in FR-2-466,492 and WO 97/35842, dihydroxyacetone (DHA), 4,4-dihydroxypyrazolin-5-one derivatives as described in EP-903,342. DHA will preferably be used.

DHA may be used in free form and/or encapsulated for example into lipid vesicles such as liposomes, described in particular in WO 97/25970.

The mono- or polycarbonyl self-tanning agents are generally present in the compositions according to the invention in proportions ranging from 0.1% to 10% by weight relative to the total weight of the composition, and preferably from 0.2% to 8% by weight relative to the total weight of the composition.

The compositions of the invention may additionally comprise conventional cosmetic adjuvants chosen in particular from fatty substances, organic solvents, thickeners, demulcents, opacifiers, stabilizers, emollients, anti-foaming agents, moisturizing agents, perfumes, preservatives, polymers, fillers, sequestrants, bactericides and/or odor absorbers, alkalinizing or acidifying agents, surfactants, emulsifiers, anti-free radical agents, antioxidants, vitamins such as vitamins E and C, α-hydroxy acids or any other ingredient normally used in cosmetics, in particular for the manufacture of vaporizable aqueous anti-sun compositions.

The fatty substances may consist of an oil or a wax or mixtures thereof, and they also comprise fatty acids, fatty alcohols and fatty acid esters. The oils may be chosen from animal, vegetable, mineral or synthetic oils and in particular from liquid paraffin, paraffin oil, volatile or nonvolatile silicone oils, isoparaffins, polyolefins, fluorinated and perfluorinated oils. Likewise, the waxes may be chosen from animal, fossil, vegetable, mineral or synthetic waxes known per se.

Among the organic solvents, there may be mentioned lower alcohols and polyols.

The thickeners may be chosen in particular from crosslinked acrylic polymers such as Carbomers, crosslinked acrylate/$C_{10}$-$C_{30}$ alkyl acrylate polymers of the Pemulen type or polyacrylate-3 sold under the name VISCOPHOBE DB 1000 by Amerchol; polyacrylamides such as the emulsion polyacrylamide, $C_{13}$-$C_{14}$ isoparaffin and laureth-7 sold under the name SEPIGEL 305 by SEPPIC, homopolymers or copolymers of AMPS such as HOSTACERIN AMPS sold by CLARIANT, guar gums and celluloses, modified or otherwise, such as hydroxypropylated guar gum, methylhydroxyethylcellulose and hydroxypropylmethylcellulose, xanthan gum, nanometric silicas of the Aerosil type.

The emulsifying agents or emulsion stabilizers may be chosen from nonionic, anionic or cationic surfactants. Among the emulsion stabilizers, there will be used more particularly polymers of isophthalic acid or of sulphoisophthalic acid, and in particular copolymers of phthalate/sulphoisophthalate/glycol (for example diethylene glycol/phthalate/isophthalate/1,4-cyclohexanedimethanol) sold under the names "Eastman AQ polymer" (AQ35S, AQ38S, AQ55S, AQ48 Ultra) by the company Eastman Chemical.

Of course, those skilled in the art will be careful to choose the possible additional compound or compounds cited above and/or their quantities such that the advantageous properties intrinsically attached to the combination [photoprotective system+microbeads of porous silica] in accordance with the invention are not, or not substantially, impaired by the addition(s) envisaged.

The compositions according to the invention may be prepared according to techniques well known to persons skilled in the art, intended for the preparation of vaporizable formulations.

The compositions according to the invention are preferably provided in the form of a simple or complex emulsion (O/W, W/O, O/W/O or W/O/W) such as a cream or a milk, and more particularly in the form of a lotion.

More preferably, the compositions according to the invention are provided in the form of an oil-in-water or water-in-oil emulsion.

When it is an emulsion, the aqueous phase thereof may comprise a nonionic vesicular dispersion prepared according to known methods (Bangham, Standish and Watkins, J. Mol. Biol. 13, 238 (1965), FR-2-315,991 and FR-2-416,008).

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLE 1

An anti-sun formulation A according to the invention capable of being packaged as a nonaerosol or aerosol spray and capable of being dispensed in the form of fine particles was prepared.

| FORMULATION A | QUANTITY % BY WEIGHT |
|---|---|
| Octocrylene(UVINUL N539) | 10 |
| Ethylhexyl triazone (UVINUL T150) | 1 |
| Drometrizole trisiloxane(Mexoryl XL) | 3 |
| Butyl methoxydibenzoylmethane (Parsol 1789) | 3 |
| Terephthalylidene dicamphor sulfonic acid (MEXORYL SX) | 0.5 |
| Titanium dioxide | 5 |
| $C_{12}$-$C_{15}$ alkyl benzoate | 6 |
| Jojoba oil | 1 |
| Shea butter | 1 |
| Cyclohexasiloxane (DC Fluid 246 from Dow Corning) | 5 |
| Glycerin | 6 |
| Propylene glycol | 6 |
| Microbeads of porous silica (Silica Beads SB 150 from Myoshi) | 1 |
| Copolymer of Diglycol/Cyclohexanedimethanol/ isophthalates/Sulphoisophthalates (AQ 38S from EASTMAN) | 1 |
| Polyacrylate-3 as an emulsion at 25% (VISCOPHOBE DB 1000 from Amerchol) | 0.5 |
| 0.5 Mixture of natural tocopherols and soya-bean oil | 0.2 |
| Triethanolamine | qs |
| Preservatives | qs |
| Water | qs 100 |

A comparative anti-sun formulation B was then prepared, having the same carrier as formulation A but containing no microbeads of porous silica.

For each of the compositions A and B, the sun protection factor (SPF) which was attached to it was then determined. This was determined using the in vitro method described by B. L. DIFFEY et al., in J. Soc. Cosmet. Chem. 40 127-133 (1989); this method consists in determining the monochromatic protection factors in a range of wavelengths from 290 nm to 400 nm and in calculating from them the sun protection factor according to a given mathematical equation. The measurement was carried out with a step of 1 nm on a UV-1000S apparatus from the company Labsphere, 2 mg/cm$^2$ of product being spread on the Transpore® strip.

The results (mean value corresponding to five trials) are grouped together in the Table below:

TABLE

| Composition | A (invention) with microbeads of porous silica | B (not in accordance with the invention) without microbead of porous silica |
|---|---|---|
| Mean SPF (standard deviation) | 21.5 (2.6) | 15.5 (2.8) |

These results clearly show that the addition, in a vaporizable carrier, of spherical microparticles of porous silica to a photoprotective system consisting of octocrylene, butyl methoxydibenzoylmethane, ethylhexyl triazone, Drometrizole trisiloxane, Terephthalylidene dicamphor sulphonic acid and nanopigments of TiO$_2$, makes it possible to significantly increase its sun protection factor.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A composition suited for pressurization and intended for protecting the skin and/or hair against UV radiation, wherein said composition is in the form of a simple or complex emulsion and comprises, in a cosmetically acceptable aqueous carrier:
    (a) a photoprotective system capable of screening out UV radiation, wherein the photoprotective system comprises a benzophenone UV-screening agent, a β,β'-diphenyl acrylate UV-screening agent, or a combination thereof; and
    (b) spherical microparticles of porous silica,
wherein the composition exhibits a SPF that is greater than a SPF exhibited by an identical composition that does not comprise spherical microparticles of porous silica.

2. The composition as defined by claim 1, said spherical porous silica microparticles having a mean particle size ranging from 0.5 µm to 20 µm.

3. The composition as defined by claim 2, said spherical porous silica microparticles having a mean particle size ranging from 3 μm to 15 μm.

4. The composition as defined by claim 2, said spherical porous silica microparticles having a specific surface ranging from 50 m$^2$/g to 1000 m$^2$/g.

5. The composition as defined by claim 4, said spherical porous silica microparticles having a specific surface ranging from 150 m$^2$/g to 800 m$^2$/g.

6. The composition as defined by claim 4, said spherical porous silica microparticles having a specific pore volume ranging from 0.5 ml/g to 5 ml/g.

7. The composition as defined by claim 6, wherein the composition is a vaporizable sunscreen composition, said spherical porous silica microparticles having a specific pore volume ranging from 1 ml/g to 2 ml/g.

8. The composition as defined by claim 1, said spherical porous silica microparticles comprising from 0.1% to 10% weight of said composition.

9. The composition as defined by claim 1, said spherical porous silica microparticles comprising from 0.2% to 5% weight of said composition.

10. The composition as defined by claim 1, said photoprotective system comprising one or more inorganic UV-screening pigment(s) or nanopigments or mixtures thereof.

11. The composition as defined by claim 1, said photoprotective system comprising one or more organic UV-screening agent(s) selected from the group consisting of an anthranilate UV-screening agent; a cinnamic UV-screening agent; a dibenzoylmethane UV-screening agent; a salicylic UV-screening agent, a camphor UV-screening agent; a triazine UV-screening agent; a benzotriazole UV-screening agent; a benzimidazole UV-screening agent; an imididazoline UV-screening agent; a p-aminobenzoic acid (PABA) UV-screening agent; a methylenebis(hydroxyphenylbenzotriazole) UV-screening agent; a benzoxazole UV-screening agent; a polymer UV-screening agent, a silicone UV-screening agent; an α-alkylstyrene dimer UV-screening agent; a 4,4-diarylbutadiene UV-screening agent and mixtures thereof.

12. The composition as defined by claim 1, said photoprotective system comprising one or more organic UV-screening agent(s) selected from the group consisting of ethylhexyl salicylate, ethylhexyl methoxycinnamate, octocrylene, phenylbenzimidazole sulphonic acid, benzophenone-3, benzophenone-4, benzophenone-5, n-hexyl 2-(4-diethylamino-2-hydroxybenzoyl)benzoate, 4-methylbenzylidene camphor, terephthalylidene dicamphor sulphonic, disodium phenyl dibenzimidazole tetra-sulphonate, 2,4,6-tris (diisobutyl 4'-aminobenzalmalonate)-s-triazine, anisotriazine, ethylhexyl triazone, diethylhexyl butamido triazone, methylene bis-benzotriazolyl tetramethylbutylphenol, drometrizole trisiloxane, polysilicone-1,1-dicarboxy (2,2'-dimethyl-propyl)-4,4-diphenylbutadiene, 2,4-bis-[5-1(dimethylpropyl) benzoxazol-2-yl-(4-phenyl)-imino]-6-(2-ethylhexyl)-imino-1,3,5-triazine and mixtures thereof.

13. The composition as defined by claim 10, said photoprotective system comprising one or more coated or uncoated metal oxide pigment(s) or nanopigments(s).

14. The composition as defined by claim 13, said photoprotective system comprising one or more pigment(s) or nanopigments(s) of titanium, iron, zinc, zirconium or cerium.

15. The composition as defined by claim 1, said photoprotective system comprising from 0.1% to 30% by weight of said composition.

16. The composition as defined by claim 1, said photoprotective system comprising from 0.5% to 15% by weight of said composition.

17. The composition as defined by claim 1, said photoprotective system composition further comprising at least one tanning agent.

18. The composition as defined by claim 17, said at least one tanning agent comprising at least one mono- or polycarbonyl compound.

19. The composition as defined by claim 18, said at least one tanning agent being selected from the group consisting of an isatin tanning agent, an alloxan tanning agent, a ninhydrin tanning agent, a glyceraldehyde tanning agent, a mesotartaric aldehyde tanning agent, a glutaraldehyde tanning agent, an erythrulose tanning agent, a pyrazolin-4,5-dione tanning agent, a dihydroxyacetone (DHA), 4,4-dihydroxypyrazolin-5-one tanning agent and mixtures thereof.

20. The composition as defined by claim 19, said tanning agent comprising DHA.

21. The composition as defined by claim 17, said at least one tanning agent comprising from 0.1% to 10% by weight of said composition.

22. The composition as defined by claim 17, said at least one tanning agent comprising from 0.2% to 8% by weight of said composition.

23. The composition as defined by claim 1, said composition further comprising at least one cosmetic additive or adjuvant selected from the group consisting of a fatty substance, an organic solvent, a thickener, a demulcent, an opacifier, a stabilizer, an emollient, an anti-foaming agent, a moisturizing agent, a perfume, a preservative, a polymer, a filler, a sequestrant, a bactericide, an odor absorber, an alkalinizing agent, an acidifying agent, a surfactant, an emulsifier, an anti-free radical agent, an antioxidant, a vitamin, an α-hydroxy acid and mixtures thereof.

24. The composition as defined by claim 1, said composition further comprising at least one polymer of isophthalic acid or of sulphoisophthalic acid.

25. The composition as defined by claim 24, said at least one polymer of isophthalic acid or of sulphoisophthalic acid comprising a copolymer of phthalate/sulphoisophthalate/glycol or a copolymer of diethylene glycol/phthalate/isophthalate/1,4-cyclohexanedimethanol.

26. The composition as defined by claim 1, said composition comprising an oil-in-water or water-in-oil emulsion.

27. The composition as defined by claim 1, wherein the photoprotective system comprises octocrylene, benzophenone-3, or a combination thereof.

28. A device comprising (A) a reservoir confining at least one composition intended for protecting the skin and/or hair against UV radiation, and (B) means to place said composition under pressure, wherein said composition is in the form of a simple or complex emulsion and comprises, in a cosmetically acceptable aqueous carrier:
(a) a photoprotective system capable of screening out UV radiation, wherein the photoprotective system comprises a benzophenone UV-screening agent, a β,β'-diphenyl acrylate UV-screening agent, or a combination thereof; and
(b) spherical microparticles of porous silica,
wherein the composition exhibits a SPF that is greater than a SPF exhibited by an identical composition that does not comprise spherical microparticles of porous silica.

29. The device as defined by claim 28, said spherical porous silica microparticles having a mean particle size ranging from 0.5 μm to 20 μm.

30. The device as defined by claim 29, said spherical porous silica microparticles having a mean particle size ranging from 3 μm to 15 μm.

31. The device as defined by claim 29, said spherical porous silica microparticles having a specific surface ranging from 50 m²/g to 1000 m²/g.

32. The device as defined by claim 31, said spherical porous silica microparticles having a specific surface ranging from 150 m²/g to 800 m²/g.

33. The device as defined by claim 31, said spherical porous silica microparticles having a specific pore volume ranging from 0.5 ml/g to 5 ml/g.

34. The device as defined by claim 33, said spherical porous silica microparticles having a specific pore volume ranging from 1 ml/g to 2 ml/g.

35. The device as defined by claim 28, said spherical porous silica microparticles comprising from 0.1% to 10% weight of said composition.

36. The device as defined by claim 28, said spherical porous silica microparticles comprising from 0.2% to 5% weight of said composition.

37. The device as defined by claim 28, said photoprotective system comprising one or more inorganic UV-screening pigment(s) or nanopigments(s) or mixtures thereof.

38. The device as defined by claim 28, said photoprotective system further comprising one or more organic UV-screening agent(s) selected from the group consisting of an anthranilate UV-screening agent; a cinnamic UV-screening agent; a dibenzoylmethane UV-screening agent; a salicylic UV-screening agent; a camphor UV-screening agent; a triazine UV-screening agent; a benzotriazole UV-screening agent; a benzimidazole UV-screening agent; an imidodazoline UV-screening agent; a p-aminobenzoic acid (PABA) UV-screening agent; a methylenebis(hydroxyphenylbenzotriazole) UV-screening agent; a benzoxazole UV-screening agent; a screening polymer UV-screening agent, a screening silicone UV-screening agent; an α-alkylstyrene dimer UV-screening agent; a 4,4-diarylbutadiene UV-screening agent and mixtures thereof.

39. The device as defined by claim 28, said photoprotective system comprising one or more organic UV-screening agent(s) selected from the group consisting of ethylhexyl salicylate, ethylhexyl methoxycinnamate, octocrylene, phenylbenzimidazole sulphonic acid, benzophenone-3, benzophenone-4, benzophenone-5, n-hexyl 2-(4-diethylamino-2-hydroxybenzoyl)benzoate, 4-methylbenzylidene camphor, terephthalylidene dicamphor sulphonic, disodium Phenyl dibenzimidazole tetra-sulphonate, 2,4,6-tris(diisobutyl 4'-aminobenzalmalonate)-s-triazine, anisotriazine, ethylhexyl triazone, diethylhexyl butamido triazone, methylene bis-benzotriazolyl tetramethylbutylphenol, drometrizole trisiloxane, polysilicone-1,1-dicarboxy (2,2'-dimethyl-propyl)-4,4-diphenylbutadiene, 2,4-bis-[5-1(dimethylpropyl)benzoxazol-2-yl-(4-phenyl)-imino]-6-(2-ethylhexyl)-imino-1,3,5-triazine and mixtures thereof.

40. The device as defined by claim 37, said photoprotective system comprising one or more coated or uncoated metal oxide pigment(s) or nanopigments(s).

41. The device as defined by claim 40, said photoprotective system comprising one or more pigment(s) or nanopigments(s) of titanium, iron, zinc, zirconium or cerium.

42. The device as defined by claim 28, said photoprotective system comprising from 0.1% to 30% by weight of said composition.

43. The device as defined by claim 28, said photoprotective system comprising from 0.5% to 15% by weight of said composition.

44. The device as defined by claim 28, where (B) comprises at least one propellant.

45. The device as defined by claim 28, said composition further comprising at least one tanning agent.

46. The device as defined by claim 45, said at least one tanning agent comprising at least one mono- or polycarbonyl compound.

47. The device as defined by claim 46, said at least one tanning agent being selected from the group consisting of an isatin tanning agent, an alloxan tanning agent, a ninhydrin tanning agent, a glyceraldehyde tanning agent, mesotartaric aldehyde tanning agent, a glutaraldehyde tanning agent, an erythrulose tanning agent, a pyrazolin-4,5-dione tanning agent derivatives, a dihydroxyacetone (DHA), 4,4-dihydroxypyrazolin-5-one tanning agent and mixtures thereof.

48. The device as defined by claim 47, said at least one tanning agent comprising DHA.

49. The device as defined by claim 46, said at least one tanning agent comprising from 0.1% to 10% by weight of said composition.

50. The device as defined by claim 46, said at least one tanning agent comprising from 0.2% to 8% by weight of said composition.

51. The device as defined by claim 28, said composition further comprising at least one cosmetic additive or adjuvant selected from the group consisting of a fatty substance, an organic solvent, a thickener, a demulcent, an opacifier, a stabilizer, an emollient, an anti-foaming agent, a moisturizing agent, a perfume, a preservative, a polymer, a filler, a sequestrant, a bactericide, an odor absorber, an alkalinizing agent, an acidifying agent, a surfactant, an emulsifier, an anti-free radical agent, an antioxidant, a vitamin, an α-hydroxy acid and mixtures thereof.

52. The device as defined by claim 28, said composition further comprising at least one polymer of isophthalic acid or of sulphoisophthalic acid.

53. The device as defined by claim 52 said at least one polymer of isophthalic acid or of sulphoisophthalic acid comprising a copolymer of phthalate/sulphoisophthalate/glycol or a copolymer of diethylene glycol/phthalate/isophthalate/1,4-cyclohexanedimethanol.

54. The device as defined by claim 28, said composition comprising an oil-in-water or water-in-oil emulsion.

55. The device as defined by claim 28, wherein the photoprotective system comprises octocrylene, benzophenone-3, or a combination thereof.

56. A method for UV-photoprotecting the skin and/or hair against the damaging effects of UV radiation, comprising spraying thereon the composition as defined by claim 1.

* * * * *